United States Patent
Cramer et al.

(10) Patent No.: US 8,343,121 B2
(45) Date of Patent: Jan. 1, 2013

(54) OSTOMY POUCH APPLIANCE

(75) Inventors: Kathryn E. Cramer, Manasquan, NJ (US); Matthew Dawson, Hillsborough, NJ (US); Tinh Nguyen-DeMary, Milltown, NJ (US)

(73) Assignee: ConvaTec Technologies, Inc., Las Vegas, NV (US)

( * ) Notice: Subject to any disclaimer, the term of this patent is extended or adjusted under 35 U.S.C. 154(b) by 351 days.

(21) Appl. No.: 12/450,714

(22) PCT Filed: Apr. 8, 2008

(86) PCT No.: PCT/US2008/059628
§ 371 (c)(1),
(2), (4) Date: Oct. 8, 2009

(87) PCT Pub. No.: WO2008/124716
PCT Pub. Date: Oct. 16, 2008

(65) Prior Publication Data
US 2010/0114045 A1 May 6, 2010

Related U.S. Application Data

(60) Provisional application No. 60/910,680, filed on Apr. 9, 2007.

(51) Int. Cl.
*A61F 5/445* (2006.01)
*A61F 5/442* (2006.01)
(52) U.S. Cl. ........................................ 604/344; 604/334
(58) Field of Classification Search ........... 604/332–345
See application file for complete search history.

(56) References Cited

U.S. PATENT DOCUMENTS

| 2,366,059 | A | * | 12/1944 | Schunk | 604/334 |
| 2,380,740 | A | * | 7/1945 | Fenwick | 604/334 |
| 2,595,934 | A | * | 5/1952 | Ginsburg | 604/342 |
| 2,902,036 | A | * | 9/1959 | Perry | 604/334 |
| 3,557,790 | A | * | 1/1971 | Hauser | 604/342 |
| 3,612,053 | A | * | 10/1971 | Pratt | 604/338 |
| 3,618,606 | A | | 11/1971 | Brown | |
| 3,759,260 | A | * | 9/1973 | Nolan et al. | 604/333 |
| 3,878,847 | A | * | 4/1975 | Marsan | 604/338 |
| 3,908,658 | A | * | 9/1975 | Marsan | 604/336 |
| 4,387,713 | A | * | 6/1983 | Calanni | 604/333 |
| 4,411,659 | A | * | 10/1983 | Jensen et al. | 604/332 |
| 4,460,359 | A | * | 7/1984 | Fenton | 604/277 |
| 4,468,227 | A | * | 8/1984 | Jensen | 604/327 |
| 4,479,818 | A | * | 10/1984 | Briggs et al. | 55/385.4 |
| 4,516,974 | A | * | 5/1985 | Davis | 604/333 |
| 4,553,967 | A | * | 11/1985 | Ferguson et al. | 604/317 |
| 4,561,858 | A | * | 12/1985 | Allen et al. | 604/336 |

(Continued)

FOREIGN PATENT DOCUMENTS
EP 0042973 1/1982
(Continued)

*Primary Examiner* — Melanie Hand
*Assistant Examiner* — Paula Craig
(74) *Attorney, Agent, or Firm* — Stuart E. Krieger (57) ABSTRACT

An ostomy appliance comprises an ostomy pouch having front wall, a rear wall with a stomal aperture, and an adhesive body fitment secured or securable around the stomal aperture. At least a portion of the adhesive of the body fitment is moldable. The front wall of the pouch comprises an access aperture providing access through the pouch interior for molding the adhesive. The access aperture is closable by a closure panel attachable over said access aperture by a peelable/resealable adhesive.

20 Claims, 7 Drawing Sheets

U.S. PATENT DOCUMENTS

| | | | | |
|---|---|---|---|---|
| 4,681,574 A * | 7/1987 | Eastman | | 604/344 |
| 4,834,731 A * | 5/1989 | Nowak et al. | | 604/339 |
| 5,096,503 A * | 3/1992 | Wellman | | 134/22.18 |
| 5,496,296 A * | 3/1996 | Holmberg | | 604/336 |
| 5,591,144 A * | 1/1997 | Smith et al. | | 604/327 |
| 5,690,622 A * | 11/1997 | Smith et al. | | 604/333 |
| 5,722,965 A * | 3/1998 | Kuczynski | | 604/344 |
| 5,769,831 A * | 6/1998 | Freeman et al. | | 604/332 |
| 5,785,695 A * | 7/1998 | Sato et al. | | 604/339 |
| 5,865,819 A * | 2/1999 | Cisko et al. | | 604/339 |
| 5,951,532 A * | 9/1999 | Olsen | | 604/332 |
| 5,976,118 A * | 11/1999 | Steer | | 604/332 |
| 6,332,879 B1 * | 12/2001 | Nielsen et al. | | 604/344 |
| 6,485,476 B1 * | 11/2002 | von Dyck et al. | | 604/332 |
| 6,569,134 B1 * | 5/2003 | Leise et al. | | 604/332 |
| 6,840,924 B2 | 1/2005 | Buglin et al. | | |
| 7,029,464 B2 * | 4/2006 | Fenton | | 604/338 |
| 7,306,581 B2 * | 12/2007 | Falconer et al. | | 604/332 |
| 2003/0004477 A1 * | 1/2003 | Nielsen et al. | | 604/336 |
| 2004/0006320 A1 | 1/2004 | Buglino | | |
| 2004/0059306 A1 | 3/2004 | Tsai | | |
| 2004/0087917 A1 * | 5/2004 | Barakat et al. | | 604/317 |
| 2004/0143230 A1 * | 7/2004 | Hansen et al. | | 604/333 |
| 2004/0193122 A1 | 9/2004 | Cline | | |
| 2005/0096611 A1 * | 5/2005 | Stoyer et al. | | 604/332 |
| 2005/0113770 A1 * | 5/2005 | Pedersen et al. | | 604/332 |
| 2005/0143696 A1 * | 6/2005 | Pedersen et al. | | 604/332 |
| 2005/0177119 A1 * | 8/2005 | Tsai | | 604/332 |
| 2006/0074389 A1 * | 4/2006 | Montgomery | | 604/332 |
| 2006/0258997 A1 * | 11/2006 | Belt | | 604/345 |
| 2009/0118686 A1 * | 5/2009 | Playdon | | 604/332 |
| 2010/0114044 A1 * | 5/2010 | Cramer et al. | | 604/332 |
| 2011/0213321 A1 * | 9/2011 | Fattman et al. | | 604/344 |
| 2011/0213322 A1 * | 9/2011 | Cramer et al. | | 604/344 |

FOREIGN PATENT DOCUMENTS

| | | |
|---|---|---|
| WO | WO2004/084777 | 10/2004 |
| WO | WO2006/035014 | 4/2006 |

\* cited by examiner

OSTOMY POUCH APPLIANCE

This application is a national stage of PCT/US2008/059628, filed Apr. 8, 2008, and claims priority to U.S. Provisional Patent Application No. 60/910,680 filed Apr. 9, 2007.

The present invention relates to an ostomy appliance comprising an ostomy pouch. In one non-limiting form, the invention relates to an appliance including a moldable adhesive. In another non-limiting form, the invention relates to a so-called one-piece appliance in which an adhesive body fitment is permanently attached to the pouch, although the invention may also be used with a two-piece appliance in which the adhesive body fitment is separably attachable to the pouch.

BACKGROUND OF THE INVENTION

Modern ostomy appliances are commonly attached to the body by means of an adhesive body fitment. The adhesive body fitments most commonly used are designed to have a predetermined, fixed shape. The wearer cuts the central opening of the adhesive fitment to match his or her stoma size and shape, using scissors to cut along guidance lines that are pre-printed on the adhesive for certain standard sizes.

U.S. Pat. No. 6,840,924 describes an improved ostomy appliance including a moldable adhesive, in which at least a portion of the adhesive can be manually shaped by the wearer, to provide a custom fit around the stoma. This alternative way of customizing the wafer offers the prospect of a better fit around the stoma than that obtainable by cutting along standard size guidelines. Achieving a good fit is desirable in order to reduce the exposure of the peristomal skin to stool exiting the stoma. Peristomal skin may be quite sensitive, and vulnerable to irritation or infection when contacted by stool. Stool exiting the stoma may contain digestive juices from the body, and such juices can also attack the peristomal skin resulting in excoriation. However, all stomas have different sizes and shapes. The advantage of a moldable adhesive as taught in U.S. Pat. No. 6,840,924 is that the user can mold the adhesive to closely match the exact size and shape of the stoma.

In a form in which the appliance of U.S. Pat. No. 6,840,924 is implemented as a two-piece ostomy appliance, the wearer is able to access the moldable adhesive on the non-body-contacting side, when the pouch is separated from the body fitment. This can enable the wearer to mold the adhesive with the body fitment in place around the stoma. However, when implemented as a one-piece appliance, the wearer can only access the moldable adhesive from the body-contacting side, and before the body fitment is secured to the body. This means that the shape and size of the aperture might not be as accurate as with a two-piece ostomy appliance.

WO-A-2004/084777 and WO-A-2006/035014 describe one-piece ostomy pouches in which an adhesive wafer is attached to the pouch using two different types of attachment extending in complementary first and second arcs that together extend completely around the stoma aperture. In the first arc, the wafer is permanently attached. In the second arc, the wafer is initially unattached or is releasably attachable. The second arc is said to permit the pouch to be folded away from the wafer in the region of the second arc, allowing access through the gap between the wafer and the pouch. This can enable access to facilitate cutting the adhesive, or fitting a separate sealing member, or removal and fitting of a separate disposable inner pouch. Some embodiments also feature an inspection hatch in the pouch wall to enable inspection of the stoma with the pouch in situ. The pouch is like a hybrid between a one-piece appliance (first arc of permanent attachment) and a two-piece appliance (second arc initially unattached or releasably attachable). However, unless the second arc is made very large, the appliance does not give complete unhindered access to the adhesive on all sides of the stoma aperture. It may be difficult for an elderly or non-dextrous person to use the appliance. Additionally, depending on the design, such a pouch construction might have vulnerabilities in the seal between the faceplate and the pouch at (i) the points at where the first and second arcs meet, and/or (ii) at the folding notches or creases of the stiffening ring, in view of the discontinuities which are inevitable at these points.

In devising the present invention, the inventors have appreciated that it would be desirable to provide an ostomy pouch appliance in which access to a moldable adhesive can be improved. More generally, it would be desirable to provide an ostomy pouch appliance in which access to the stomal area may be improved.

SUMMARY OF THE INVENTION

Broadly speaking, one aspect of the present invention provides an ostomy appliance comprising an ostomy pouch having a stomal aperture, and an adhesive body fitment secured or securable around the stomal aperture. At least a portion of the adhesive of the body fitment is moldable. The body fitment has an adhesive body-facing side for adhesively contacting the body, and a non-body-facing side that faces towards the pouch interior. The pouch comprises a closable opening configured for providing access through the pouch interior to the non-body-facing side of the adhesive.

With such an arrangement, the closable opening allows the ostomate (or some other person such as a nurse or other caregiver) to access the adhesive of the body fitment, even when the pouch is worn on the body.

The term "moldable" as used herein is intended to mean generally that the adhesive may be any of deformed or extruded or reshaped by hand. In a preferred form, the moldable adhesive portion is a moldable as a deformable adhesive sheet, meaning that the wafer retains generally sheet-like properties (in contrast to an extrudable form, for example), but the adhesive wafer may be molded by bending or flexing the adhesive wafer in the moldable region, or by rolling the adhesive wafer back on itself. Such a moldable wafer is especially configured for allowing the stomal aperture in the adhesive to be enlarged to a customized size and/or shape. The adhesive wafer may have a spring-back property such that the adhesive may tend to spring back partly towards its initial shape. Such a spring-back property may be useful for sealing around the stoma. Alternatively, the adhesive contact of the rolled back portion of the wafer may anchor the wafer stably in the molded shape without any, or with only limited, spring back.

In one embodiment, the adhesive wafer includes a constrained shape zone around the moldable region. The adhesive in the constrained zone may be integral with and/or of the same thickness as, the adhesive in the moldable region.

In one embodiment, the ostomy appliance is a one-piece item, in which the body fitment is permanently attached to the ostomy pouch. The term "permanently" as used herein is intended to mean that the body fitment is attached or attachable to the pouch in such a way that the fitment is not easily separable from the pouch without damage and/or is never intended to be separable from the pouch during normal use. Preferably, the body fitment is permanently secured around the entire circumference of the stomal aperture, to optimize the integrity of the seal between the body fitment and the ostomy pouch. With such a one-piece appliance, the closable opening allows access to the adhesive to enable the adhesive to be molded as easily and as accurately as with a two-piece appliance, either during initial fitting of the body fitment around the stoma, or once the appliance has been fitted to the body.

In an alternative embodiment, the ostomy appliance is a two-piece item, in which the body fitment is separably fastenable to the pouch (for example, by a releasable and/or resealable adhesive, or by a mechanical fastening). Even with a two-piece appliance, the closable opening may allow useful access to the adhesive, without having to remove the pouch from the body fitment.

The closable opening may take a variety of forms. A particularly preferred form is an aperture (referred to herein as an access aperture) in a wall of the pouch that faces the stoma aperture. For example, the access aperture may be in a front wall of the pouch, the stomal aperture being in a rear wall of the pouch. The access aperture preferably overlaps, at least partly, the stoma aperture. The access aperture may be approximately the same shape as the stomal aperture (e.g., round), but the access aperture may have a different shape as desired. The access aperture may be approximately the same size as the stomal aperture, or the access aperture may be larger than, or smaller than, the stoma aperture. The access aperture may be closed by a closure such as a sheet or panel of material fastenable around, or over, the access aperture. The closure may conveniently be fastenable by means of a peelable and resealable adhesive, that allows the adhesive bond to be peeled free, and remade, a plurality of times, so that the access aperture may be opened and reclosed. The adhesive may be carried on the pouch (e.g., on a flange faceplate surrounding the access aperture), or on the closure, or both. The closure may incorporate a flatus vent.

In other forms, the closable opening may comprise a flap portion of the pouch wall. Additionally or alternatively, the closable opening may be implemented in a seam of the pouch.

In another aspect, the invention provides an ostomy appliance comprising an ostomy pouch having a front wall and a rear wall, a stomal aperture formed in the rear wall, an access aperture formed in the front wall, and a closure for openably closing the access aperture. The closure incorporates a flatus vent and a deodorizing filter. In use, should the filter become soiled, the user can replace the filter by removing the closure, and fitting instead a replacement closure with a new filter.

The access aperture preferably overlaps, at least partly, the stoma aperture. The access aperture may be approximately the same shape and/or size as the stomal aperture, or the second aperture may be larger than, or smaller than, the stoma aperture, and/or of a different shape.

While features believed to be of special significance have been identified above and the appended claims, the Applicants claim protections for any novel feature or idea described herein and/or illustrated in the drawings, whether or not emphasis has been placed thereon.

DETAILED DESCRIPTION OF THE PREFERRED EMBODIMENTS

Referring to FIGS. 1-4, a first embodiment illustrates a one-piece ostomy appliance 10 comprising an ostomy pouch 12 and a body fitment 14 permanently attached to the ostomy pouch 12. The ostomy pouch 12 may be any of a colostomy pouch, a urostomy pouch and an ileostomy pouch.

The ostomy pouch 12 generally comprises a rear wall 16 and a front wall 18. The front and rear walls 16, 18 are made of flexible plastics film that is generally impermeable to liquid and gas. A suitable film includes, for example, a laminate of one or more layers of ethylene vinyl acetate (EVA), and one more layers of a gas barrier material, such as poly(vinylidene chloride) (PVDC). The walls 16, 18 are welded together around a mutual periphery 20. The ostomy pouch 12 optionally further comprises a deodorizing filter and vent (not shown) for deodorizing and venting flatus.

Figure 1:
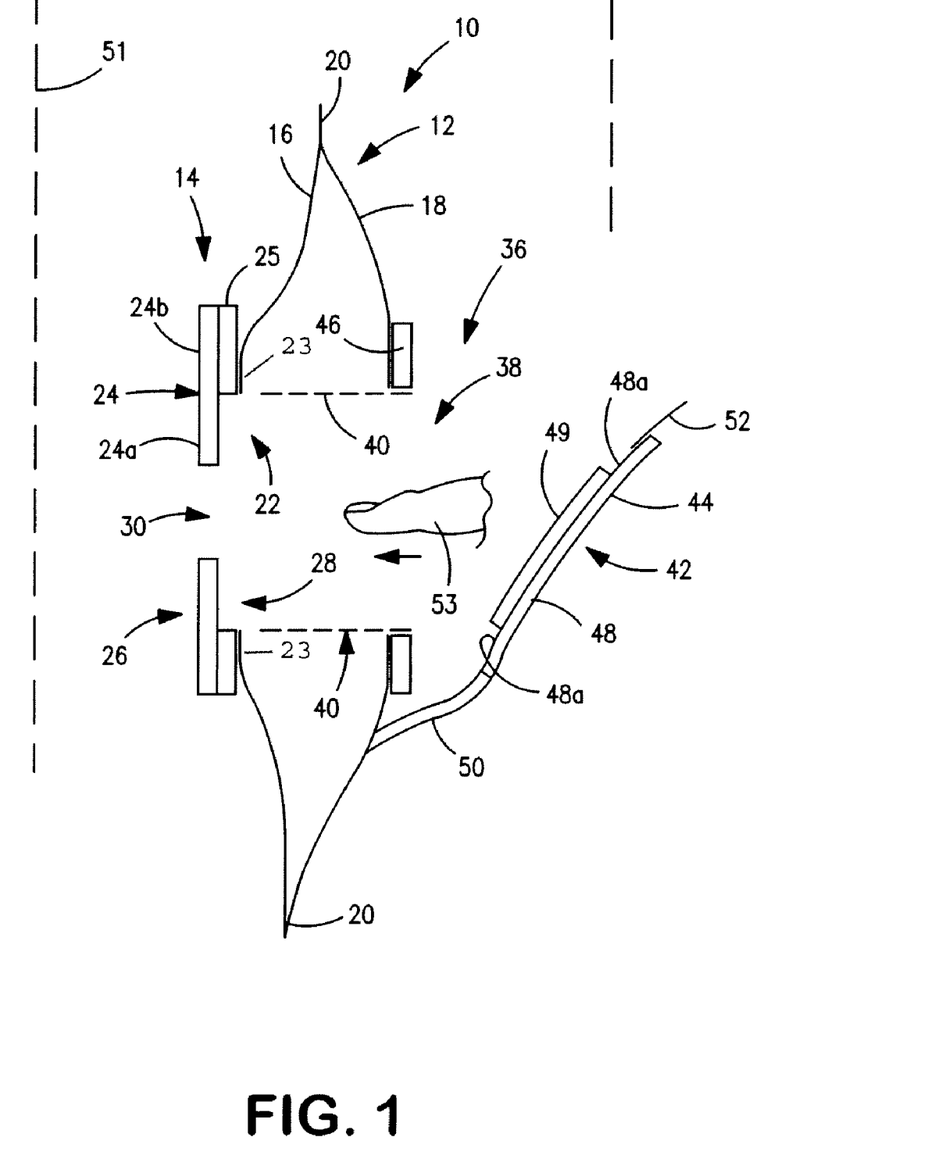
FIG. 1 is a schematic side-sectional view through a first embodiment of ostomy pouch, in the form of a one-piece appliance worn on a body, and shown with the access aperture open.
Figure 3:
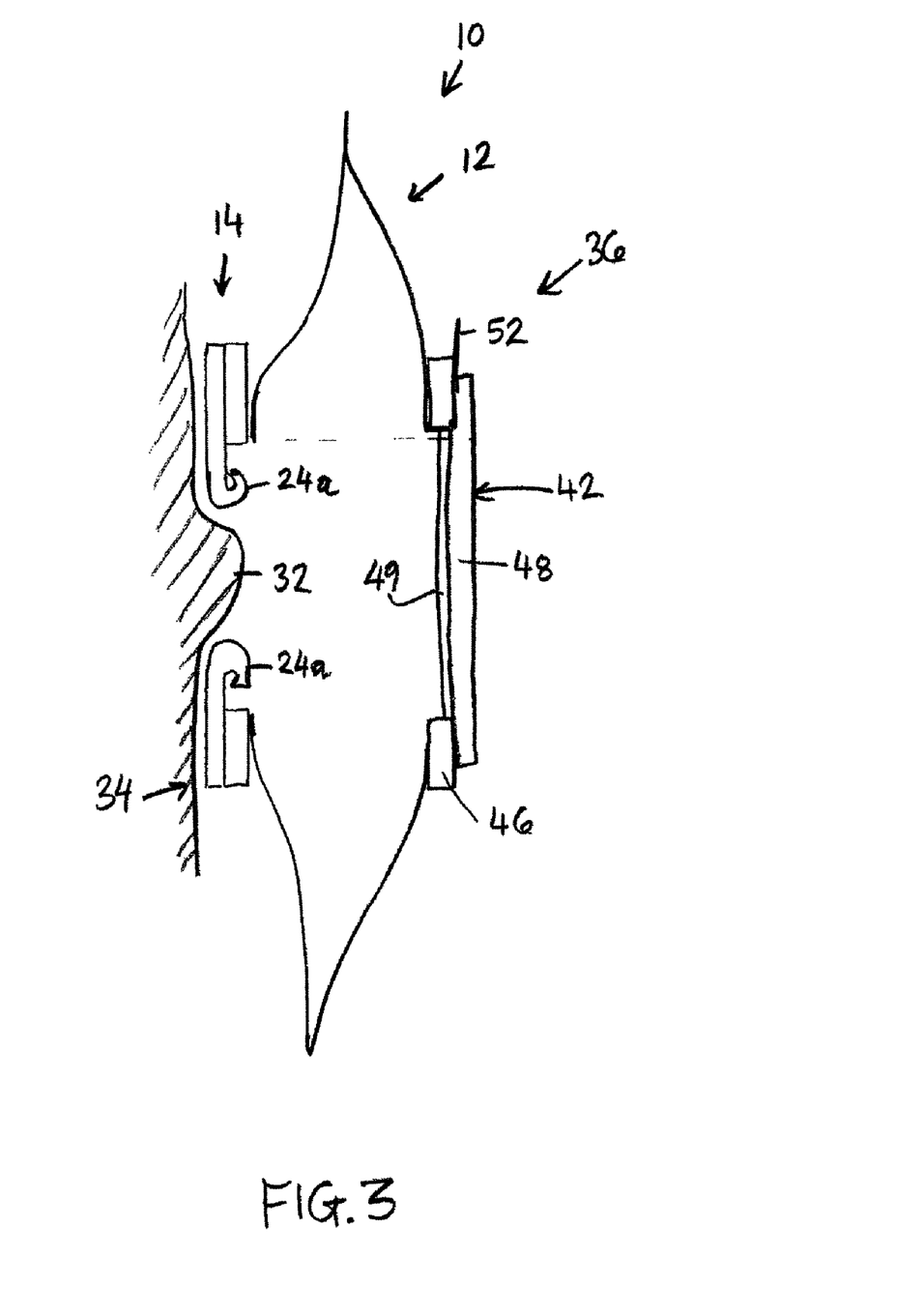
FIG. 3 is a schematic side-sectional view similar to FIG. 1, but showing the access aperture closed.

The rear wall 16 comprises a stomal aperture 22 around which the body fitment 14 is attached to the rear wall 16. The body fitment 14 is attached, for example, by a suitable strong adhesive or weld in a region 23 surrounding the stomal aperture 22. The permanent attachment extends around the entire periphery of the stomal aperture 22, to provide continuous seal properties, and thus optimize the integrity of the seal between the ostomy pouch 12 and the body fitment 14. The body fitment 14 includes a wafer of a skin compatible adhesive 24. The adhesive 24 generally has a body-facing side 26 for facing towards and contacting the skin, and a non-body-facing side 28 that faces away from the skin, and instead faces towards the interior of the ostomy pouch 12. In this embodiment, the adhesive 24 is of a moldable type, in which at least a portion of the adhesive 24 (such at least an inner peripheral region 24a) is moldable or shapeable by manual manipulation, to enable the size and/or the shape of the central starter aperture 30 to be customized to match the size and/or shape of the ostomate's stoma 32 (FIG. 3). A close or snug fit around the stoma 32 is highly desirable, in order to protect the ostomate's peristomal skin 34 from irritation and excoriation by contact with stool exuding from the stoma 32. The adhesive 24 may, for example, be of the type described in the aforementioned U.S. Pat. No. 6,840,924. Such an adhesive 24 is configured in a moldable wafer form to enable the adhesive to be shaped while retaining a sheet-like form. The adhesive 24 comprises a laminate structure including (i) plural layers of adhesive, and/or (ii) at least one layer of adhesive reinforced by at least one layer of plastics film. The aperture in the adhesive 24 can be expanded to a customized shape and/or size by bending and rolling the adhesive 24 back on itself around the aperture, as illustrated in FIG. 3. Alternatively, the adhesive 24 may be of a flowable or extrudable mass type (not shown). In either case, in the present embodiment, the inner peripheral region 24a of the adhesive 24 is integral with a constrained region 24b of the same adhesive 24, that has a more constrained shape. The two regions 24a, 24b optionally have the same thickness. The constrained region 24b may be defined by backing or reinforcing member 25. The member 25 may be flexible, or it may be stiffer than the adhesive 24.

The member 25 may be generally planar (e.g., a planar ring, as illustrated), or it may be non-planar, e.g., flared or frusto-conical.

The ostomy pouch 12 comprises a closable opening (depicted generally at 36) for enabling a person (for example, the ostomate, or a nurse or other caregiver) to access the adhesive 24 from the non-body-facing side 28, through the interior of the ostomy pouch 12. The closable opening 36 is distinct from the stomal aperture 22. Access from the non-body-facing side 28 is highly advantageous, because it allows the person to manipulate the adhesive 24 (or at least the inner peripheral region 24a) (i) prior to fitting of the ostomy appliance 10 to the body, e.g., during preparation of the ostomy pouch 12; and/or (ii) during the fitting of the ostomy appliance 10 to the body to verify a good fit, and allow minor adjustments of the adhesive 24 as necessary, and/or (ii) after the ostomy appliance 10 has been fitted to the body. This is a highly significant advantage compared to a conventional one-piece ostomy appliance, in which access from the non-body-facing side 28 is impossible because, in a conventional one-piece ostomy appliance, the non-body-facing side 28 is permanently covered by the pouch wall material.

Figure 2:
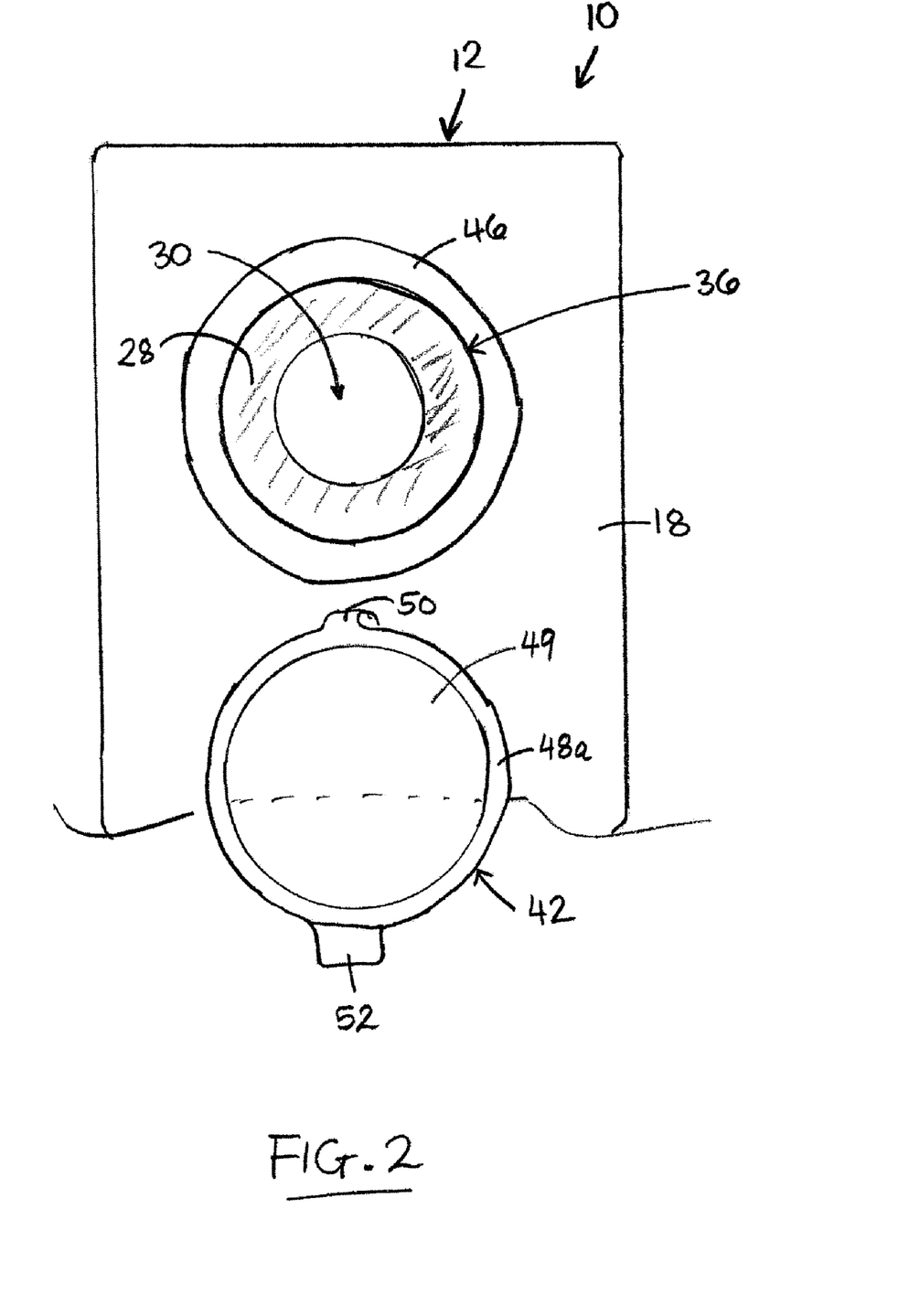
FIG. 2 is a schematic front view of the pouch of FIG. 1, and additionally showing the closure folded fully open.

In the illustrated embodiment, the closable opening 36 is provided in the form of an access aperture 38 in the front wall 18 of the ostomy pouch 12. The access aperture 38 is, for example, generally the same shape as the stomal aperture 22, such as round. However, the access aperture 38 may have a different shape, if desired. The access aperture 38 is, for example, of approximately the same size as the stomal aperture 22 (as indicated by the broken lines 40). However, the access aperture 38 may be smaller or larger, as desired. The access aperture 38 at least partly overlaps the stomal aperture 22, for ease of access to the stomal region and the adhesive 24.

The ostomy appliance 10 further comprises an access closure 42 for openably closing the access aperture 38. In the present embodiment, the access closure 42 generally comprises a sheet or panel 44 that is attachable over the access aperture 38 to seal the access aperture 38 closed. The panel 44 is attachable by means of a resealable adhesive that allows the adhesive bond to be peeled apart, and remade, a plurality of times. In order to protect the front wall 18 from risk of damage caused by peeling the panel 44 open, the ostomy pouch 12 optionally comprises a flange or faceplate 46 on the front wall 18 for contacting the panel 44. The resealable adhesive may be carried on the faceplate 46 and/or on the panel 44. In the illustrated embodiment, the adhesive is carried on the panel 44, and the faceplate 46 is made of a non-adhesive, generally tough but flexible plastics film. The faceplate 46 is larger than the panel 44, to avoid any adhesion complications should the panel 44 be slightly out of position or alignment. The panel 44 comprises a layer of foam material 48 carrying the adhesive, and a layer 49 of gas impermeable plastics. The impermeable layer 49 is dimensioned to be larger than the access aperture 38, but smaller than the overall size of the foam material 48, to leave a peripheral circumferential (e.g., annular) region 48a of the foam material 48 exposed. The region 48a is the adhesive region of the panel 44 for contacting the faceplate 46.

Also in the present embodiment, the panel 44 is attached captively to the ostomy pouch 12, for example, by a living hinge 50 between the panel 44 and the ostomy pouch 12. The living hinge 50 is formed by an extension of the flexible foam material 48 attached to the front wall 18 or to the faceplate 46. Alternatively, such a living hinge 50 could be formed by an extension of the faceplate 46 or a flap (not shown) attached to the front wall 18. The living hinge 50 is formed at the bottom edge of the panel 44 when the pouch is viewed in a normally upright orientation, so that the panel 44 will fold downwardly in use, and thereby avoiding the panel 44 closing accidentally under gravity if the panel 44 were to fold open in a different direction. The panel 44 further comprises a tab 52 generally opposite the living hinge 50, by which the panel 44 can be grasped for peeling the panel 44 open by a downward movement.

The ostomy appliance 10 may be supplied to the user in a sealed package, depicted schematically at 51. The package 51 may be sterilized and/or hermetically sealed. In the form supplied to the user, the body-fitment 14 is permanently sealed to the ostomy pouch 12 all around the periphery of the stoma aperture 22 in the ostomy pouch 12. Equivalent packaging 51 may be used with other embodiments, even if not illustrated explicitly in the drawings to avoid clutter. One or removable release sheets (not shown) may be provided initially protecting the adhesive surface on the body-facing side 26 of the body fitment 14, and/or the adhesive surface on the non-body-facing side 28 that faces the pouch interior.

Referring to FIGS. 1 and 2, in order to prepare the ostomy appliance 10 prior to fitting to an ostomate, the panel 44 is peeled down to open the access aperture 38, and expose the non-body-facing side 28 of the adhesive 24 through the interior of the ostomy pouch 12. A person may insert his or her fingers (as indicated at 53) through the access aperture 38, to manipulate the adhesive 24 by folding or rolling the inner peripheral region 24a towards the pouch interior. The ability to access the adhesive 24 from the non-body-facing side 28 enables the person to accurately mold the adhesive 24 to precisely fit the unique size and shape of the stoma 32, thereby obtaining an excellent seal around the stoma 32. Even once the ostomy appliance 10 is in its worn position, the person can still access the adhesive 24 to make minor adjustments to the molded shape, and achieve an optimum fit.

The ostomy pouch 12 is then fitted to the peristomal skin, such that the stoma 32 enters the stomal aperture 22 molded in the adhesive 24. The fit of the adhesive 24 can be inspected through the access aperture 38.

Thereafter, (FIGS. 3 and 4) the panel 44 is resealed in order to close the access aperture 38. The adhesive bond of the access panel 44 is sufficiently strong to ensure that the panel 44 remains firmly closed in use of the ostomy pouch 12. The impermeable layer 49 blocks leakage of flatus through the panel 44, thereby ensuring that the closable opening 36 does not compromise the integrity of the ostomy pouch 12 in use.

Figure 4:
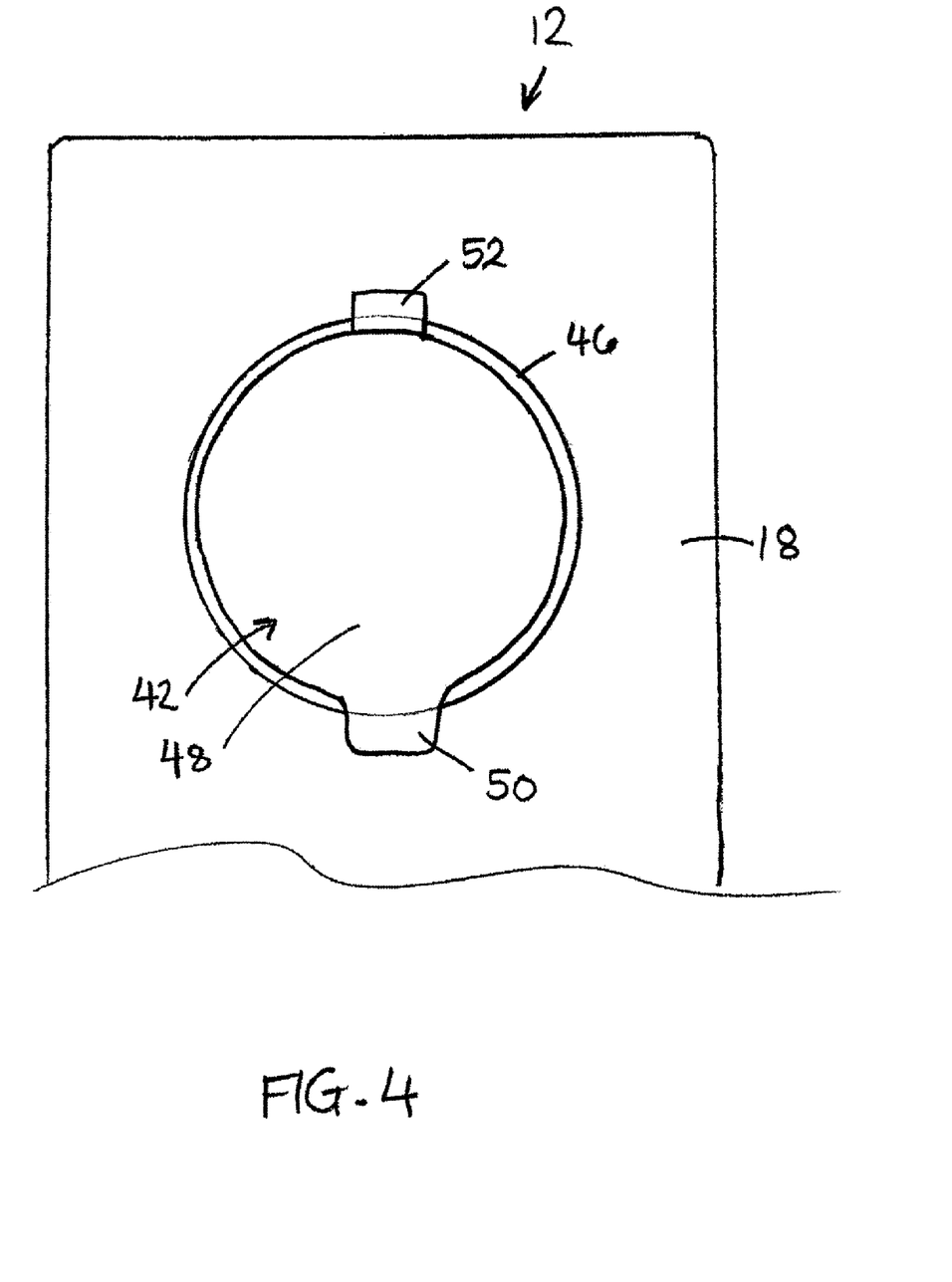
FIG. 4 is a schematic front view of the pouch of FIG. 3.

The panel 44 also permits the ostomate, or another person such a nurse or other caregiver, to access the stoma 32 or the adhesive 24 even while the ostomy appliance 10 is being worn. The panel 44 can be peeled open at any time desired, for example, to effect minor adjustments to the molded shape of the adhesive 24, or for inspection or cleaning of the stoma 32, or to administer medicaments directly on to the stoma tissue. Once the process has been completed, the panel 44 is reclosed to continue normal use of the ostomy pouch 12. Release material may be provided on the inside of the ostomy pouch 12 and/or on the inside of the panel 44 to help prevent the panel 44 from sticking to the inside surface of the moldable adhesive 24.

Figure 5:
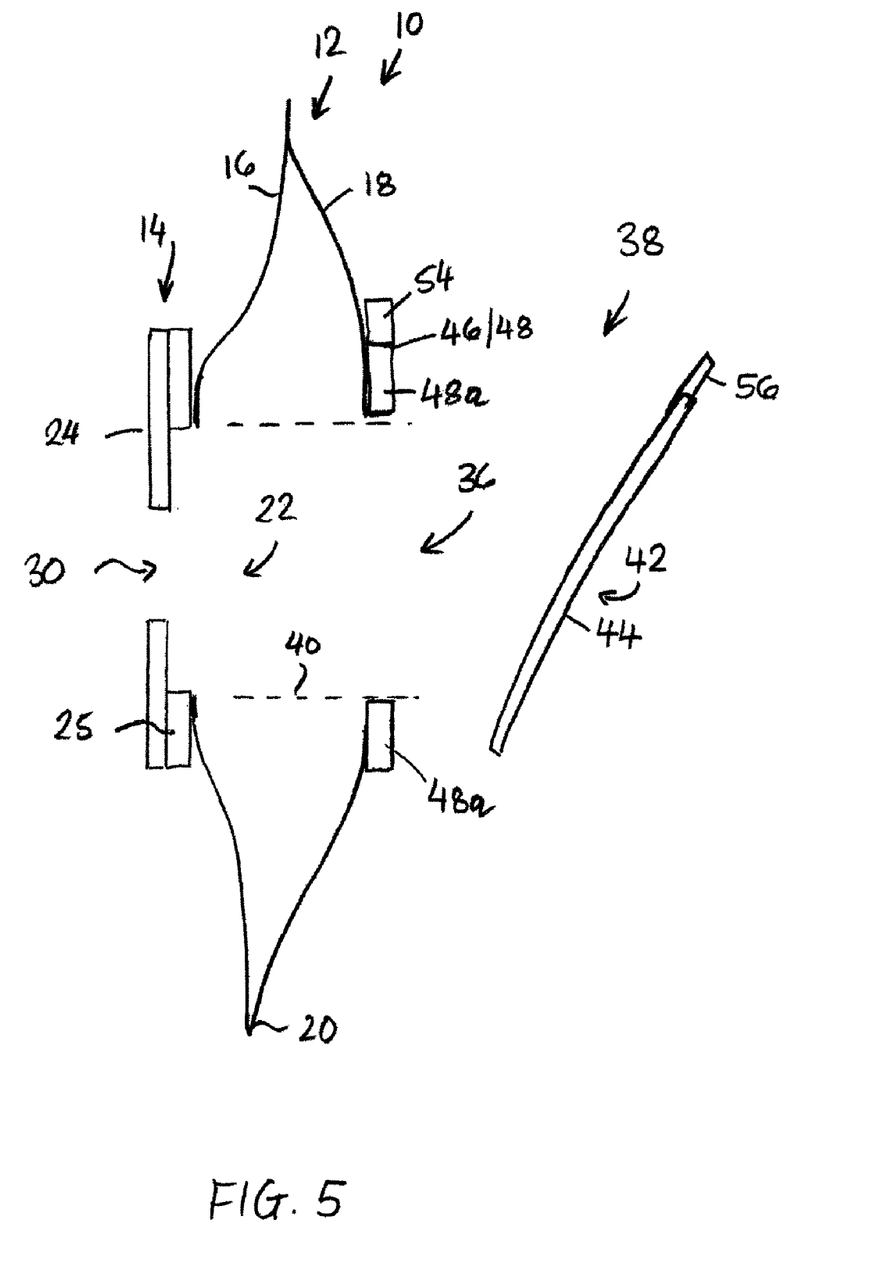
FIG. 5 is a schematic side-sectional view through a second embodiment of ostomy pouch, with the access aperture open.
Figure 6:
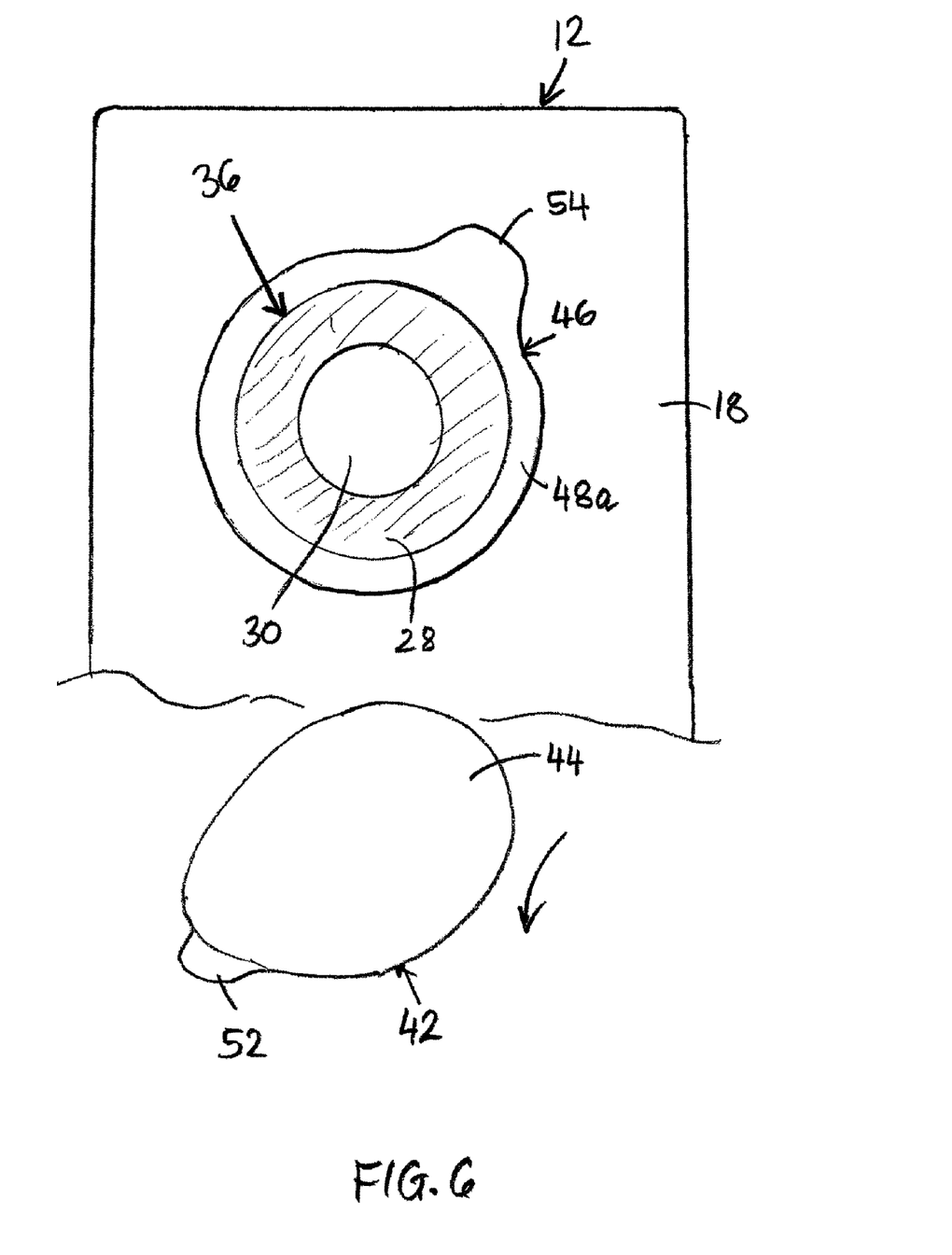
FIG. 6 is a schematic front view of the second embodiment, with the closure being removed.

FIGS. 5 and 6 illustrate a second embodiment of ostomy appliance 10 and ostomy pouch 12. The second embodiment is similar to the first embodiment except in the detail of the access aperture 38 and access closure 42. In the second embodiment, the adhesive is carried by the faceplate 46. The faceplate 46 is constructed of the adhesive foam material 48 as used in the closure panel 44 of the first embodiment. The foam material 48 defines a generally annular adhesive region 48a, and an optional, non-adhesive grip tab 54. The access closure 42 comprises a panel 44 of a generally tough yet flexible plastics film optionally provided with a grip tab 56, for peeling the panel 44 from the faceplate 46.

In the second embodiment, the panel 44 is illustrated to be distinct from the pouch 12, although, if desired, the panel 44 could be attached to the ostomy pouch 12 captively, as in the first embodiment.

Figure 7:
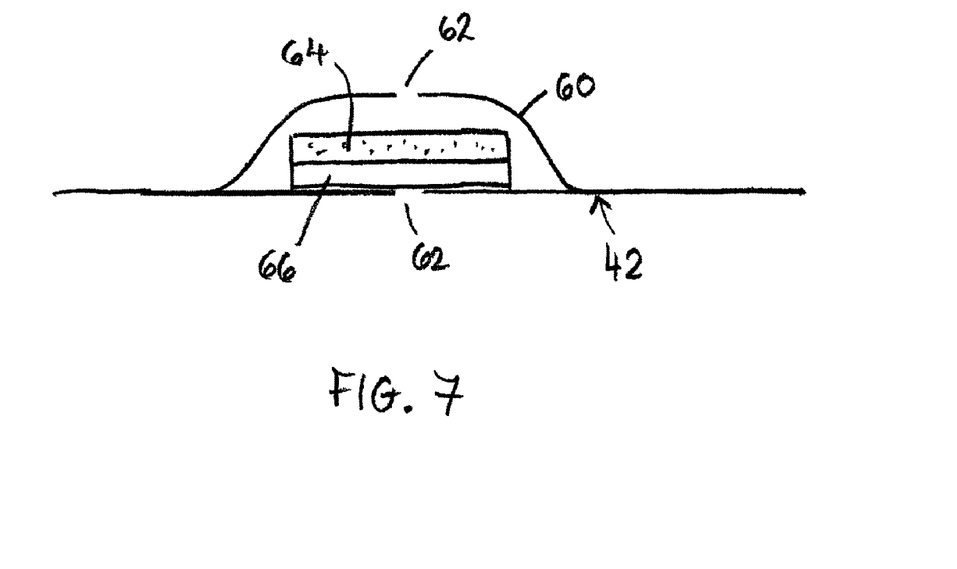
FIG. 7 is a schematic side-sectional view through a closure panel having an integrated filter in a third embodiment.

FIG. 7 illustrates a third embodiment, which is a modification of the access closure 42 usable in the first or second embodiment. In the third embodiment, a flatus vent assembly (identified generally by the numeral 60) is integrated into the access closure 42. Various configurations of flatus vent assembly 60 are possible. In the illustrated embodiment, the flatus vent assembly 60 generally comprises one or more vent apertures 62 in the access closure 42, a deodorizing filter 64 communicating with the vent aperture 62 for deodorizing flatus exiting through the vent aperture 62, and a protection stage 66 for protecting the deodorizing filter 64 from contact by solid and liquid stool. The protection stage 66 may be integrated into the deodorizing filter 64 and/or may itself comprise one or more gas-permeable barrier components (not shown). Although the flatus vent assembly 60 is illustrated generally to be on the side of the access closure 42 that faces away from pouch interior, one or more (or all) components of the flatus vent assembly may be placed on the inner face of the access closure 42.

Integrating the flatus vent assembly 60 into the access closure 42 may be advantageous because:

(i) from a manufacturing view, the flatus vent assembly 60 can be made separately from the ostomy pouch 12, as a smaller flatus vent assembly 60, leading to easier production and/or production at a manufacturing different location or using different plant; and (ii) from a user's view, particularly with the second embodiment, the arrangement allows replacement of a used or soiled flatus vent assembly 60 simply by using a new access closure 42. Thus, should the deodorizing filter 64 become soiled, or blocked, or otherwise stop functioning prematurely, the user may be able to discard the access closure 42 with the malfunctioning deodorizing filter 64, and replace it by a fresh access closure 42 with a fresh deodorizing filter 64. The user may therefore continue wearing the ostomy appliance 10 for its full wear-life.

Figure 8:
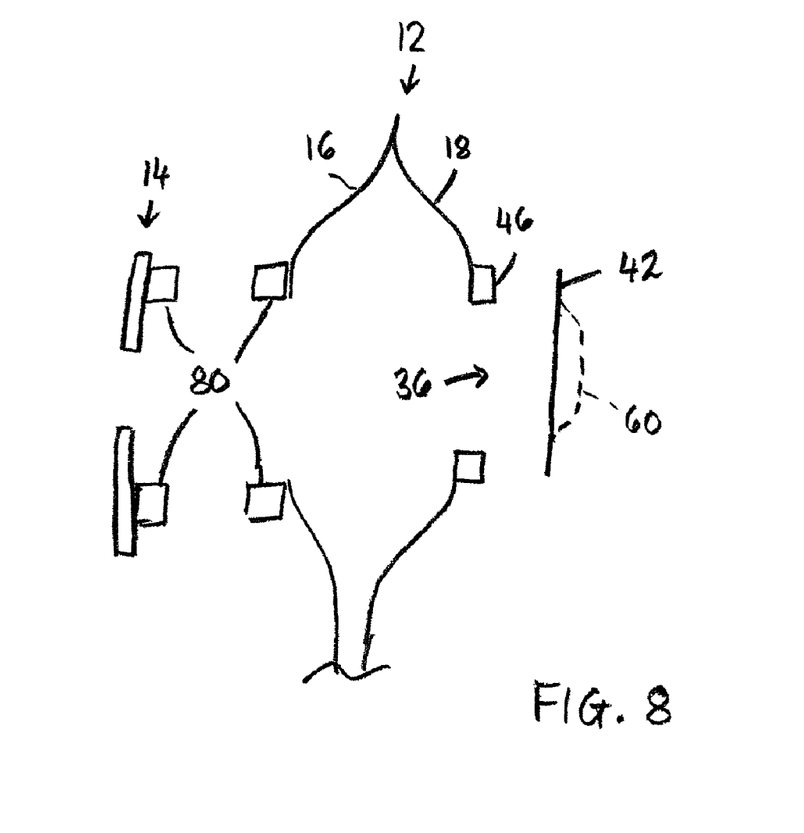
FIG. 8 is a schematic side-sectional view of a fourth embodiment in the form of a two-piece appliance.

FIG. 8 illustrates a fourth embodiment of the invention. The main difference in the fifth embodiment is that the ostomy appliance 10 is a two-piece appliance. The adhesive body fitment 14 is releasably fastenable to the ostomy pouch 12 by means of an ostomy coupling 80. The ostomy coupling 80 may be a mechanical type (e.g., using inter-engaging locking rings) or an adhesive type (e.g., using a peelable and resealable adhesive). The ostomy coupling 80 permits the ostomy pouch 12 to be completely detached from the body fitment 14, so that a replacement pouch may be fitted when desired. The access aperture 38 and access closure 42 of the fourth embodiment may be similar to those of any preceding embodiment, but are especially advantageous when using the third embodiment.

As explained above, even with a two-piece appliance as in the fourth embodiment, the invention may enable the ostomate or another person (such as a nurse or other caregiver) to have access to the stoma 32 even while the ostomy appliance 10 is worn on the body. When this embodiment is combined with the third embodiment, replacement of the flatus vent assembly 60 is also facilitated without having to replace the ostomy pouch 12 itself.

It will be appreciated that the foregoing description is illustrative of preferred forms of the invention, and that many modifications, improvements and equivalents are possible that are within the scope of the claimed coverage of the invention.

We claim:

1. An ostomy appliance comprising:

a. an ostomy pouch having (i) an interior space; (ii) a stomal aperture communicating with the interior space; (ii) a closable opening distinct from the stomal aperture, and communicating with the interior space; and b. an adhesive body fitment attached to the ostomy pouch along a region of permanent attachment that extends entirely around the stomal aperture so that the body fitment is permanently sealed to the ostomy pouch all around the stomal aperture, the body fitment having (i) an adhesive body-facing surface and (ii) a non-body-facing surface; and the body fitment including adhesive having a moldable region integral with a constrained region, the adhesive having a more constrained shape in the constrained region than in the moldable region;

wherein the closable opening of the ostomy pouch is configured for providing when open access to and direct contact with the non-body-facing surface of the adhesive, through the pouch interior, to enable direct molding of the moldable region of the adhesive from the non-body-facing surface of the adhesive;

wherein the pouch comprises a front wall and a rear wall, said stomal aperture being provided in said rear wall, and said closable opening comprising an access aperture provided in said front wall, and said access aperture at least partly overlaps said stomal aperture; and further comprising a flatus vent formed in said closable opening, and a deodorizing filter carried by said closable opening.

2. The ostomy appliance according to claim 1, wherein the adhesive includes a starter hole in the moldable region, the moldable region permitting the starter hole to be molded into a stoma aperture.

3. The ostomy appliance according to claim 1, wherein the constrained region is defined by a backing that is stiffer than the adhesive.

4. The ostomy appliance according to claim 1, wherein the moldable region of the adhesive of the body fitment is moldable as an adhesive deformable sheet.

5. The ostomy appliance according to claim 1, wherein the moldable region of the adhesive of the body fitment is moldable as a homogenous mass.

6. The ostomy appliance according to claim 1, wherein said access aperture is the same shape as the stomal aperture.

7. The ostomy appliance according to claim 1, wherein said access aperture is the same size as the stomal aperture, or bigger.

8. The ostomy appliance according to claim 1, further comprising a closure for releasably closing said access aperture.

9. The ostomy appliance according to claim 8, wherein said closure comprises a panel attachable over said access aperture.

10. The ostomy appliance according to claim 9, wherein said panel is attachable by a peelable adhesive.

11. The ostomy appliance according to claim 10, wherein said adhesive is carried on at least one of said panel and a faceplate on said pouch.

12. The ostomy appliance according to claim 8, wherein said closure comprises a portion of the front wall of the pouch.

13. An ostomy appliance comprising:
a. an ostomy pouch, the pouch comprising:
   i. a rear wall having a stomal aperture; the ostomy appliance having a moldable adhesive region surrounding the stomal aperture, the moldable adhesive region having a body side and non-body-side, and
   ii. a front wall having an access aperture at least partly overlapping said stomal aperture;
b. said appliance further comprising:
   i. a closure for openably closing said access aperture, the closure providing when open access to and direct contact with the non-body side of the adhesive for molding of the moldable adhesive region from the non-body side, said closure comprising a flatus vent and carrying a deodorising filter for deodorising flatus passing through said vent.

14. The ostomy appliance according to claim 13, wherein said access aperture is the same shape as the stomal aperture.

15. The ostomy appliance according to claim 13, wherein said access aperture is the same size as said stomal aperture, or bigger.

16. The ostomy appliance according to claim 13, wherein said closure comprises a panel attachable over said access aperture.

17. The ostomy appliance according to claim 16, wherein said panel is attachable by a peelable adhesive.

18. The ostomy appliance according to claim 17, wherein said adhesive is carried on at least one of said panel and a faceplate on said pouch.

19. The ostomy appliance according to claim 13, wherein at least a portion of said closure is removable and replaceable by a new closure having a new deodorising filter without destroying the remainder of the pouch.

20. A method of preparing an ostomy appliance for application to a patient and applying the ostomy appliance to the patient, the steps comprising:
providing an ostomy pouch having (i) an interior space; (ii) a stomal aperture communicating with the interior space; (ii) a closable opening distinct from the stomal aperture, and communicating with the interior space; and
an adhesive body fitment attached to the ostomy pouch, the body fitment having (i) an adhesive body-facing surface and (ii) a non-body-facing surface; and the adhesive body fitment including adhesive at least a region of which is moldable;
accessing the moldable region of the adhesive, on the non-body-facing side, through the closable opening of the ostomy pouch distinct from the stomal aperture of the ostomy pouch;
molding a stoma receiving aperture in the moldable region of the adhesive by directly manipulating the moldable region through the closable opening and the pouch interior;
and adhering the adhesive body fitment to the patient.

* * * * *